US010500278B2

(12) United States Patent
Abazeed

(10) Patent No.: US 10,500,278 B2
(45) Date of Patent: Dec. 10, 2019

(54) GENOSPECIFIC RADIOSENSITIZATION

(71) Applicant: THE CLEVELAND CLINIC FOUNDATION, Cleveland, OH (US)

(72) Inventor: Mohamed Abazeed, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 800 days.

(21) Appl. No.: 14/832,159

(22) Filed: Aug. 21, 2015

(65) Prior Publication Data

US 2016/0053323 A1    Feb. 25, 2016

Related U.S. Application Data

(60) Provisional application No. 62/040,580, filed on Aug. 22, 2014.

(51) Int. Cl.
*A61K 41/00*    (2006.01)
*C12Q 1/6883*    (2018.01)
(Continued)

(52) U.S. Cl.
CPC ...... *A61K 41/0038* (2013.01); *A61K 31/7088* (2013.01); *C12Q 1/6883* (2013.01);
(Continued)

(58) Field of Classification Search
CPC ............ C12Q 1/6883; C12Q 2600/156; G01N 33/6893; A61K 31/7088; A61K 41/0038; A61N 2005/1098
See application file for complete search history.

(56) References Cited

U.S. PATENT DOCUMENTS

2002/0040155 A1* 4/2002 Holton ................. C07D 305/14
549/510
2004/0138195 A1* 7/2004 Denny ................. C07D 257/00
514/185
(Continued)

OTHER PUBLICATIONS

Ooi et al. "CUL3 and NRF2 Mutations Confer and NRF2 Activation Phenotype in a Sporadic Form of Papillary Renal Cell Carcinoma" Cancer Res; 73(7); 1-8. (2013) Published OnlineFirst Jan. 30, 2013; DOI: 10.1158/0008-5472.CAN-12-3227.*
(Continued)

*Primary Examiner* — Kaylee R Wilson
(74) *Attorney, Agent, or Firm* — Tarolli, Sundheim, Covell & Tummino LLP

(57) ABSTRACT

A method of treating a subject who has been diagnosed with cancer is described. The method includes characterizing the radiation-susceptibility of the subject by detecting a mutation in an NRF2 pathway protein in suitable sample obtained from the subject and treating the subject with radiation therapy if the subject is characterized as being radiation-susceptible, or treating the subject with radiation therapy and a radiosensitizing agent if the subject is characterized as being radioresistant. A method of determining if a subject has a history of tobacco smoking is also described that includes analyzing an NRF2 pathway protein to determine if a mutation is present in suitable sample obtained from the subject and characterizing the subject as having a history of tobacco smoking if a genetic fingerprint consistent with tobacco exposure is identified.

7 Claims, 6 Drawing Sheets

(51) Int. Cl.
*A61K 31/7088* (2006.01)
*G01N 33/68* (2006.01)
*A61N 5/10* (2006.01)

(52) U.S. Cl.
CPC .. *G01N 33/6893* (2013.01); *A61N 2005/1098* (2013.01); *C12Q 2600/156* (2013.01)

(56) References Cited

U.S. PATENT DOCUMENTS

| | | | |
|---|---|---|---|
| 2010/0047368 A1* | 2/2010 | Biswal | A61K 48/00 424/649 |
| 2010/0255117 A1 | 10/2010 | Biswal et al. | |
| 2010/0273171 A1* | 10/2010 | Jorgensen | C12Q 1/6895 435/6.14 |
| 2011/0136246 A1* | 6/2011 | Shibata | C12Q 1/6886 436/94 |
| 2014/0363496 A1* | 12/2014 | Ghoroghchian | A61K 9/5146 424/450 |
| 2015/0057486 A1 | 2/2015 | Abazeed et al. | |

OTHER PUBLICATIONS

Zhou et al. ("Nrf2 is a potential therapeutic target in radioresistance in human cancer" Critical Reviews in Oncology/Hematology 88 (2013) 706-715).*

Abazeed, Mohamed E., et al. "Integrative radiogenomic profiling of squamous cell lung cancer." Cancer research 73.20 (2013): 6289-6298.

Chapman, Paul B., et al. "Improved survival with vemurafenib in melanoma with BRAF V600E mutation." New England Journal of Medicine 364.26 (2011): 2507-2516.

Druker, Brian J., et al. "Efficacy and safety of a specific inhibitor of the BCR-ABL tyrosine kinase in chronic myeloid leukemia." New England Journal of Medicine 344.14 (2001): 1031-1037.

Hast, Bridgid E., et al. "Cancer-derived mutations in KEAP1 impair NRF2 degradation but not ubiquitination." Cancer research 74.3 (2014): 808-817.

Karar, Jayashree, and Amit Maity. "Modulating the tumor microenvironment to increase radiation responsiveness." Cancer biology & therapy 8.21 (2009): 1994-2001.

Komatsu, Masaaki, et al. "The selective autophagy substrate p62 activates the stress responsive transcription factor Nrf2 through inactivation of Keap1." Nature cell biology 12.3 (2010): 213-223.

Kwok, Pui-Yan, and Xiangning Chen. "Detection of single nucleotide polymorphisms." Current issues in molecular biology 5 (2003): 43-60.

Lynch, Thomas J., et al. "Activating mutations in the epidermal growth factor receptor underlying responsiveness of non-small-cell lung cancer to gefitinib." New England Journal of Medicine 350.21 (2004): 2129-2139.

Malhotra, Deepti, et al. "Global mapping of binding sites for Nrf2 identifies novel targets in cell survival response through ChIP-Seq profiling and network analysis." Nucleic acids research 38.17 (2010): 5718-5734.

Nagase, Takahiro, et al. "Prediction of the coding sequences of unidentified human genes. IV. The coding sequences of 40 new genes (KIAA0121-KIAA0160) deduced by analysis of cDNA clones from human cell line KG-1." DNA Research 2.4 (1995): 167-174.

Cancer Genome Atlas Research Network. "Comprehensive genomic characterization of squamous cell lung cancers." Nature 489.7417 (2012): 519-525.

Ota, Toshio, et al. "Complete sequencing and characterization of 21,243 full-length human cDNAs." Nature genetics 36.1 (2004): 40-45.

Rosell, Rafael, et al. "Erlotinib versus standard chemotherapy as first-line treatment for European patients with advanced EGFR mutation-positive non-small-cell lung cancer (EURTAC): a multicentre, open-label, randomised phase 3 trial." The lancet oncology 13.3 (2012): 239-246.

Shibata, Tatsuhiro, et al. "Cancer related mutations in NRF2 impair its recognition by Keap1-Cul3 E3 ligase and promote malignancy." Proceedings of the National Academy of Sciences 105.36 (2008): 13568-13573.

Taguchi, Keiko, Hozumi Motohashi, and Masayuki Yamamoto. "Molecular mechanisms of the Keap1—Nrf2 pathway in stress response and cancer evolution." Genes to Cells 16.2 (2011): 123-140.

Zaytseva, Yekaterina Y., et al. "mTOR inhibitors in cancer therapy." Cancer letters 319.1 (2012): 1-7.

Zhang, Ping, et al. "Loss of Keap1 Function in Prostate Cancer Cells Causes Chemo-and Radio-resistance and Promotes Tumor Growth." Molecular cancer therapeutics 9.2 (2010): 336.

PCT International Search Report and Written Opinion for PCT/US2015/046249, dated Nov. 19, 2015, pp. 1-14.

* cited by examiner

GENOSPECIFIC RADIOSENSITIZATION

CROSS-REFERENCE TO RELATED APPLICATIONS

This application claims priority to U.S. Provisional Patent Application Ser. No. 62/040,580, filed Aug. 22, 2014, which is incorporated herein by reference.

BACKGROUND

Wilhelm Conrad Röntgen made the salient discovery of X-rays in 1985. In January 1986, only six months later, Emil Grubbé translated this discovery for the treatment of an advanced ulcerated breast cancer using a vacuum tube. Clinical radiotherapy has made significant technical advances since its early days of inception, growing into a technology driven tertiary specialty with significant contributions to curative and palliative treatments of cancer and health care cost. As a non-invasive approach of controlling gross tumor or the eradication of microscopic residual disease, it has been incorporated into the clinical management of most solid tumors.

Radiation therapy uses ionizing radiation to control or kill malignant cells. Radiation therapy may be curative in a number of types of cancer if they are localized to one area of the body. It may also be used as part of adjuvant therapy, to prevent tumor recurrence after surgery to remove a primary malignant tumor (for example, early stages of breast cancer). Ionizing radiation works by damaging the DNA of cancerous tissue leading to cellular death. To spare normal tissues (such as skin or organs which radiation must pass through to treat the tumor), shaped radiation beams are aimed from several angles of exposure to intersect at the tumor, providing a much larger absorbed dose there than in the surrounding, healthy tissue. Radiation may be used to provide palliative treatment where a cure is not possible and the aim is for local disease control or symptomatic relief, or as therapeutic treatment, where the therapy has survival benefit and it can be curative. Most common cancer types can be treated with radiation therapy. However, a major limitation to the appropriate application of this technology is the lack of any established means by which to identify patients with cancers that are more or less likely to respond to treatment.

Emerging advances in genomic technology have enabled a cataloguing of cancer genes that have resulted in the identification of genetic alterations that contribute to onco-genesis and/or tumor progression and in some cases have led to significant therapeutic advances in subsets of cancer patients. Druker et al., N Engl J Med 344, 1031 (Apr. 5, 2001); Rosell et al., Lancet Oncol 13, 239 (March, 2012). In contrast, radiotherapy regimens are delivered based on the site of anatomic origin of disease and do not currently take into account the genetic complexity that may regulate therapeutic response. Accordingly, there remains a need for a better understanding of what patients are more likely to benefit from radiation therapy, and the identification of additional agents that can be used together with radiotherapy to sensitize cancer cells to radiation.

SUMMARY OF THE INVENTION

The present invention describes methods for characterizing subjects who could benefit from therapy with a genotype-specific radiation sensitizing agent. The invention also includes a method of treating a subject who has been diagnosed with cancer, the method comprising (a) characterizing the radiation-susceptibility of the subject by detecting a mutation in an NRF2 pathway protein in suitable sample obtained from the subject; and (b) treating the subject with radiation therapy if the subject is characterized as being radiation-susceptible, or treating the subject with radiation therapy and a radiosensitizing agent if the subject is characterized as being radioresistant.

Another aspect of the invention provides a method of determining if a subject has a history of tobacco smoking, comprising analyzing an NRF2 pathway protein to determine if a mutation is present in suitable sample obtained from the subject, and characterizing the subject as having a history of tobacco smoking if a genetic fingerprint consistent with tobacco exposure is identified.

BRIEF DESCRIPTION OF THE FIGURES

The present invention may be more readily understood by reference to the following figures, wherein.

DETAILED DESCRIPTION OF THE INVENTION

Figure 1:
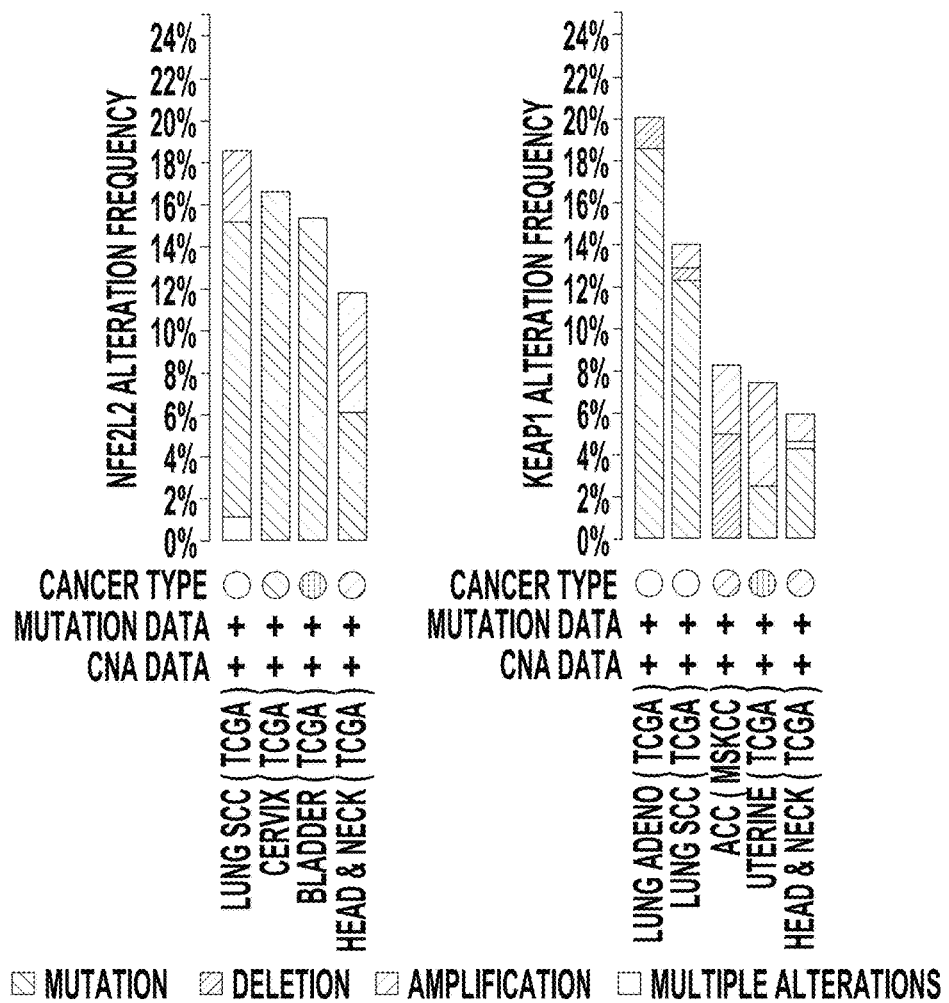
FIG. 1 provides bar graphs showing NFE2L2 and KEAP1 genetic alterations in human samples. These data indicate that NFE2L2 mutations and amplifications occur frequently in SCC of the lung whereas KEAP1 mutations and/or deletions occur frequently in adenocarcinomas of the lung.

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis). "Diagnosis" can also encompass diagnosis in the context of rational therapy, in which the diagnosis guides therapy, including initial selection of therapy, modification of therapy (e.g., adjustment of dose or dosage regimen), and the like.

As used herein, the term "prognosis" refers to a prediction of the probable course and outcome of a disease, or the likelihood of recovery from a disease. Prognosis is distinguished from diagnosis in that it is generally already known that the subject has the disease, although prognosis and diagnosis can be carried out simultaneously. In the case of a prognosis for cancer, the prognosis categorizes the relative severity of the cancer, which can be used to guide selection of appropriate therapy for the cancer.

As used herein, the terms "treatment," "treating," and the like, refer to obtaining a desired pharmacologic or physiologic effect. The effect may be therapeutic in terms of a partial or complete cure for a disease or an adverse effect attributable to the disease. "Treatment," as used herein, covers any treatment of a disease in a mammal, particularly in a human, and can include inhibiting the disease or condition, i.e., arresting its development; and relieving the disease, i.e., causing regression of the disease.

The terms "therapeutically effective" and "pharmacologically effective" are intended to qualify the amount of an agent which will achieve the goal of improvement in disease severity and the frequency of incidence over treatment of each agent by itself, while avoiding adverse side effects typically associated with alternative therapies. The effectiveness of treatment may be measured by evaluating a reduction in tumor load or decrease in tumor growth in a subject in response to the administration of anticancer agents. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

"Nucleic acids" encompass nucleotides of RNA and DNA, including cDNA (DNA transcribed from RNA template strands), genomic DNA, synthetic (e.g., chemically synthesized) DNA and chimeras of RNA and DNA. The nucleic acid may be double-stranded or single-stranded. Where single-stranded, the nucleic acid may be a sense strand or an antisense strand. The nucleic acid may be synthesized using nucleotide analogs or derivatives (e.g., inosine or phosphorothioate nucleotides). Such oligonucleotides can be used, for example, to prepare nucleic acids that have altered base-pairing abilities or increased resistance to nucleases.

A "polynucleotide" is a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein and in the appended claims, the singular forms "a", "and", and "the" include plural referents unless the context clearly dictates otherwise. Thus, for example, reference to "a sample" also includes a plurality of such samples and reference to "the KEAP1 protein" includes reference to one or more protein molecules, and so forth.

Unless defined otherwise, all technical and scientific terms used herein have the same meaning as commonly understood by one of ordinary skill in the art to which this invention belongs.

Characterizing the Radiation-Susceptibility of a Subject

In one aspect, the invention provides a method of treating a subject who has been diagnosed with cancer, the method comprising: (a) characterizing the radiation-susceptibility of the subject by detecting a mutation in an NRF2 pathway protein in suitable sample obtained from the subject; (b) treating the subject with radiation therapy if the subject is characterized as being radiation-susceptible, or treating the subject with radiation therapy and a radiosensitizing agent if the subject is characterized as being not radiation-susceptible.

Nuclear factor erythroid-2 related factor 2 (Nrf2) is a basic leucine zipper transcription factor, which regulates a transcriptional program that maintains cellular redox homeostasis and protects cells from oxidative insult. Nrf2 activates transcription of its target genes through binding specifically to the antioxidant-response element (ARE) found in those gene promoters. NRF2 protects cells and multiple tissues by coordinately up-regulating ARE-related detoxification and antioxidant genes and molecules required for the defense system. Nrf2-activation suppresses oxidative stress and inflammation and has been shown to be neuroprotective.

The Keap1-Nrf2 regulatory pathway plays a central role in the protection of cells against oxidative and xenobiotic damage. Under unstressed conditions, Nrf2 is constantly ubiquitinated by the Cul3-Keap1 ubiquitin E3 ligase complex and rapidly degraded in proteasomes. Upon exposure to electrophilic and oxidative stresses, reactive cysteine residues of Keap1 become modified, leading to a decline in the E3 ligase activity, stabilization of Nrf2 and robust induction of a battery of cytoprotective genes. Biochemical and structural analyses have revealed that the intact Keap1 homodimer forms a cherry-bob structure in which one molecule of Nrf2 associates with two molecules of Keap1 by using two binding sites within the Neh2 domain of Nrf2. This two-site binding appears critical for Nrf2 ubiquitination. In many human cancers, missense mutations in KEAP1 and NRF2 genes have been identified. These mutations disrupt the Keap1-Nrf2 complex activity involved in ubiquitination and degradation of Nrf2 and result in constitutive activation of Nrf2. Elevated expression of Nrf2 target genes confers advantages in terms of stress resistance and cell proliferation in normal and cancer cells. See Taguchi et al., Genes Cells. 2011 February; 16(2):123-40, the disclosure of which is incorporated herein by reference.

Examples of NRF2 pathway proteins include the KEAP1 (kelch-like ECH-associated protein 1) protein, CUL3 (cullin 3), NFE2L2 (nuclear factor, erythroid 2-like 2), and TP53 (tumor protein p53). The sequences of these proteins, and nucleotides encoding these proteins, are known to those skilled in the art. For example, the amino acid sequence of human KEAP1 was identified by Dhakshinamoorthy and Jaiswal in 2001, and assigned Accession No. Q14145, while the nucleotide sequence coding for KEAP1 is described by Nagase et al., DNA Res. 2 (4), 167-174 (1995), the disclosure of which is incorporated herein by reference. Likewise, the amino acid sequence of human NFE2L2 was identified in 2004 and assigned Accession No. Q16236. Ota et al., Nat. Genet. 36 (1), 40-45 (2004), the disclosure of which is incorporated herein by reference.

Figure 2:
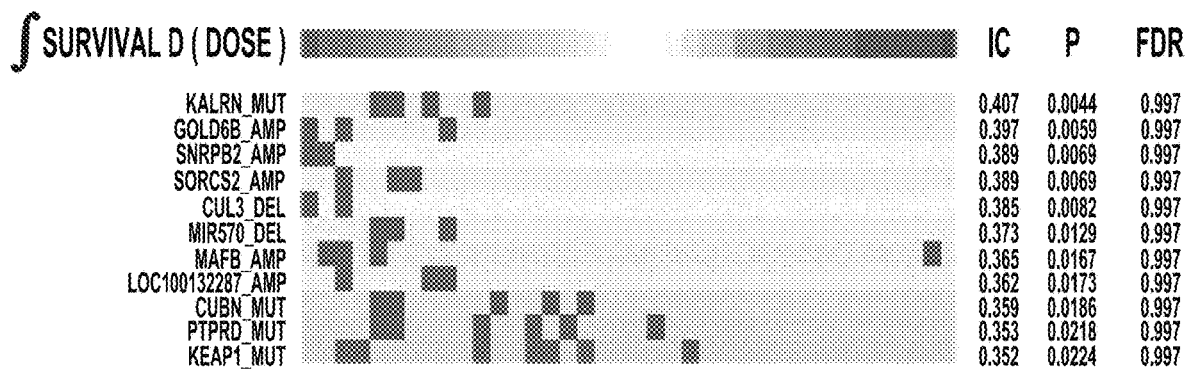
FIG. 2 provides a chart showing NRF2 activation through CUL3 and KEAP1 mutations confers radiation resistance. Thirty eight lung adenocarcinoma cell lines were subjected to radiation profiling. 1842 genomic features (mutations, deletions, amplifications) annotated by the Cancer Cell Line Encyclopedia were sorted as a function of integral survival. CUL3 deletion and KEAP1 mutation were fifth and eleventh out of 1842 genomic features as predictors of radiation resistance. IC, information component; P, p value; FDR, false discovery rate.
Figure 3:
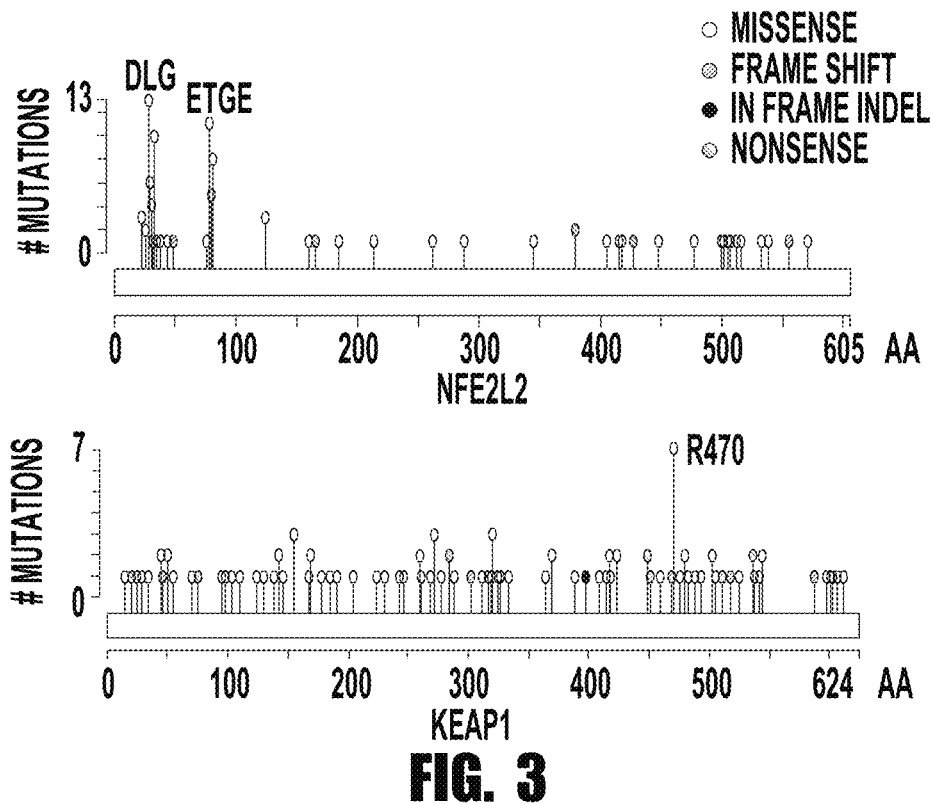
FIG. 3 provides a scheme showing NFE2L2 and KEAP1 mutations sorted by amino acid residue in samples profiled by TCGA. (top) These data reveal hot spots in mutation frequency in NFE2L2 at DLG (aa 29-31) and ETGE (aa 79-82). (bottom) KEAP1 mutations are distributed less discretely across the open reading frame with a moderate peak of frequency at R470.
Figure 4:
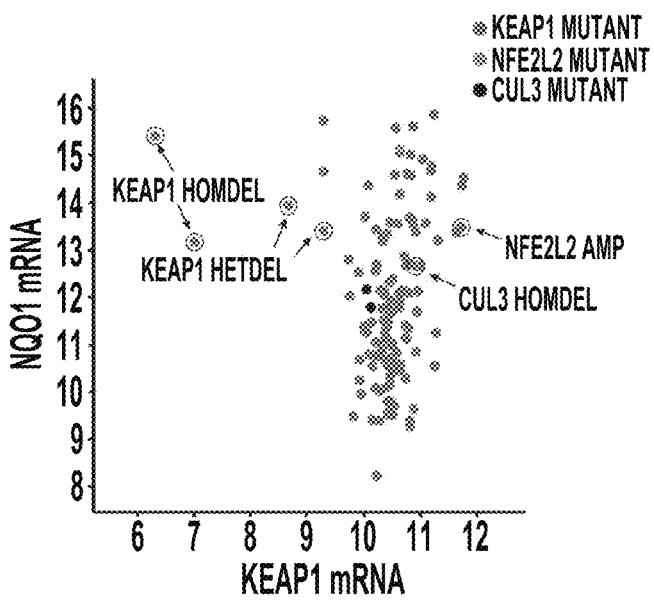
FIG. 4 provides a graph showing mRNA levels of KEAP1 and NQO1 as measured by RNA Seq are sorted by genotype. KEAP1 alterations show elevated levels of NQO1, suggesting that KEAP1 mutations result in the activation of NRF2.
Figure 5:
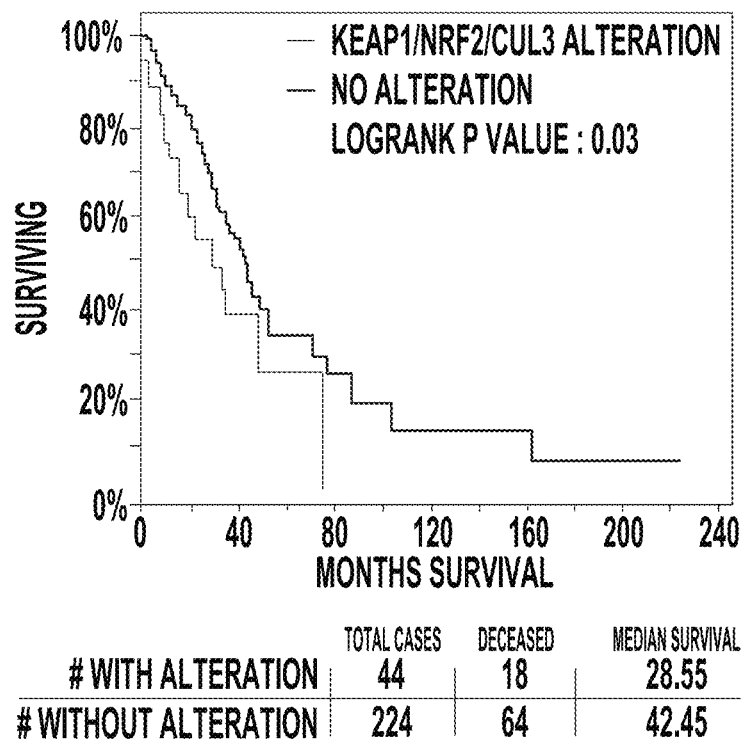
FIG. 5 provides a graph showing the Kaplan-Meier survival curves for patients with and without NRF2 pathway alterations including KEAP1 mutation and homozygous deletion, NFE2L2 mutation and amplification, and CUL3 deletion.

The inventors have shown that mutations of proteins in the NRF2 pathway can confer resistance of cancer cells to radiotherapy. A mutation consists of one or several amino acid replacements, deletions or additions or a combination thereof, that results in a change in the activity of the NRF2 pathway protein. NFE2L2 and KEAP1 mutations are frequent in malignancies of the upper aerodigestive tract and can be found in various types of cancer, as shown in FIG. 1. KEAP1 mutations are particularly common in adenocarcinomas of the lung and predict for resistance to radiation, as shown in FIG. 2. KEAP1 mutations do not cluster within discrete regions in the gene, as compared to NFE2L2 (FIG. 3). Accordingly, in some embodiments of the invention, the mutation in the KEAP1 protein is a mutation selected from Table 1. A significant subset of KEAP1 mutations are functionally silent as measured by a surrogate marker for the loss of KEAP1 function, NQO1 mRNA up-regulation, as shown in FIG. 4. Subjects whose tumors contain KEAP1 alterations have decreased overall survival compared to subjects with no alterations in the NRF2 pathway, as shown in FIG. 5.

TABLE 1

KEAP1 mutations associated with radiation resistance

| AA Change | Type | Copy # | Allele Freq (T) |
|---|---|---|---|
| A191T | Missense | diploid | 0.13 |
| S144F | Missense | hetloss | 0.18 |
| E117K | Missense | hetloss | 0.19 |
| L268P | Missense | hetloss | 0.21 |
| R470S | Missense | hetloss | 0.23 |
| R261P | Missense | hetloss | 0.27 |
| P322fs | FS ins | diploid | 0.28 |
| M503K | Missense | diploid | 0.31 |
| Q46* | Nonsense | hetloss | 0.31 |
| G524C | Missense | hetloss | 0.31 |
| R460G | Missense | hetloss | 0.37 |
| F246L | Missense | hetloss | 0.38 |
| F139L | Missense | hetloss | 0.38 |
| R470C | Missense | hetloss | 0.4 |
| A159P | Missense | hetloss | 0.42 |
| F280Y | Missense | hetloss | 0.43 |
| S102L | Missense | diploid | 0.43 |
| T142M | Missense | hetloss | 0.44 |
| I461V | Missense | diploid | 0.44 |
| D479G | Missense | hetloss | 0.48 |
| E218V | Missense | hetloss | 0.5 |
| R415C | Missense | diploid | 0.5 |
| G417E | Missense | diploid | 0.52 |
| V99L | Missense | diploid | 0.53 |
| G417R | Missense | hetloss | 0.54 |
| R470H | Missense | hetloss | 0.54 |
| Q284L | Missense | diploid | 0.55 |
| G333C | Missense | hetloss | 0.56 |
| E449* | Nonsense | diploid | 0.56 |
| G333S | Missense | hetloss | 0.58 |
| R320W | Missense | hetloss | 0.6 |
| G477fs | FS del | hetloss | 0.6 |
| V155A | Missense | hetloss | 0.63 |
| W497L | Missense | hetloss | 0.63 |
| R204P | Missense | hetloss | 0.63 |
| P278S | Missense | hetloss | 0.64 |
| W252C | Missense | gain | 0.66 |
| G570_splice3D | Splice | hetloss | 0.78 |
| G480W | Missense | hetloss | 0.83 |
| L100P | Missense | hetloss | 0.92 |

The present invention provides a method of treating a subject that has been diagnosed with cancer. The methods are also useful in the treatment of precancers and other incidents of undesirable cell proliferation. As shown in FIG. 1, mutation of NRF2 pathway proteins occurs in a variety of different types of cancer. Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of leukemia, hepatic cancer, non-small cell lung cancer, squamous cell lung cancer, colon cancer, head and neck cancer, melanoma, ovarian cancer, renal cancer, bladder cancer, prostate cancer, cervical cancer, and breast cancer. Preferred types of cancer include those resulting in solid tumors such as breast cancer, prostate cancer, lung cancer, and colon cancer. In some embodiments, the method is used to treat a subject who has been diagnosed as having lung adenocarcinoma. The genomic alterations involved in squamous cell lung cancer have been described. See Nature, 2012, 489(7414), 519-525, the disclosure of which is incorporated herein by reference.

The term "subject" for purposes of treatment includes any human or animal subject who has a disorder characterized by unwanted, rapid cell proliferation (e.g., cancer). Such disorders include, but are not limited to cancers and precancers. In some embodiments, the subject is a human or animal subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on. For example, in some embodiments, the subject has a history of tobacco smoking. Besides being useful for human treatment, the methods of the present invention are also useful for veterinary treatment of mammals, including companion animals and farm animals, such as, but not limited to dogs, cats, horses, cows, sheep, and pigs.

Mutations of NRF2 pathway proteins can be detected using a wide variety of methods known to those skilled in the art. Examples of suitable methods include direct Sanger's DNA sequencing and next-gen sequencing (e.g., cancer genome, transcriptome or exomic sequencing). Next-gen sequencing makes use of sequence by synthesis technology, in which a fluorescently labeled reversible terminator is imaged as each dNTP is added, and then cleaved to allow incorporation of the next base. Since all four reversible terminator-bound dNTPs are present during each sequencing cycle, natural competition minimizes incorporation bias, thereby providing a true base-by-base sequencing. Analysis of discrete changes in DNA sequences derived from blood and surgical specimens can be evaluated using high density single nucleotide polymorphism (SNP) arrays, such as SNP genotyping and SNP array-based kayotyping. See Kwok P Y, Chen X, Curr. Issues Mol. Biol., 5, 43-60 (2003), the disclosure of which is incorporated by reference herein, for a discussion of a variety of methods for detecting SNPs. In some embodiments, the mutation is detected using polymerase chain reaction (PCR) analysis.

Determining the Level of Nrf2 Protein

In some embodiments, the method of characterizing the radiation-susceptibility of a subject further includes determining the level of Nrf2 protein in a suitable sample (i.e., a biological sample) obtained from the subject. Cancer cell lines including genetic alteration of an NRF2 pathway protein such as NFE2L2 or KEAP1 show an elevated level of Nrf2 protein. Accordingly, this protein level can also be measured to determine if a subject is radioresistant or radiosusceptible. An elevated level of Nrf2 also characterizes the subject as being radioresistant. Analysis of Nrf2 levels therefore complements the identification of mutations in an NRF2 pathway protein, and can increase the reliability of the characterization.

In some embodiments, the level of Nrf2 protein is determined. Whether or not the level of Nrf2 protein is elevated can be evaluated by comparing the determined level to predetermined levels, the level of corresponding internal standards in the sample, or another type of control value. The level of Nrf2 protein can be determined by determining the level of the Nrf2 protein itself, or by determining level of RNA expressing the Nrf2 protein. The amount of Nrf2 protein in a biological sample can be determined, for example, using polyclonal or monoclonal antibodies that are immunoreactive with the Nrf2 protein in an immunoassay. Use of antibodies comprises contacting a sample taken from the subject with one or more of the antibodies; and assaying for the formation of a complex between the antibody and the Nrf2 protein in the sample. For ease of detection, the antibody can be attached to a substrate such as a column, plastic dish, matrix, or membrane, preferably nitrocellulose. The sample may be untreated, subjected to precipitation, fractionation, separation, or purification before combining with the antibody. Interactions between antibodies in the sample and the Nrf2 protein are detected by radiometric, colorimetric, or fluorometric means, size-separation, or precipitation. Preferably, detection of the antibody-protein or peptide complex is by addition of a secondary antibody that is coupled to a detectable tag, such as for example, an enzyme, fluorophore, or chromophore. Formation of the complex is indicative of the presence and level of Nrf2 protein in the sample.

Antibodies immunospecific for the Nrf2 protein may be made and labeled using standard procedures and then employed in immunoassays to detect the Nrf2 protein in a sample. Suitable immunoassays include, by way of example, immunoprecipitation, particle immunoassay, immunonephelometry, radioimmunoassay (RIA), enzyme immunoassay (EIA) including enzyme-linked immunosorbent assay (ELISA), sandwich, direct, indirect, or competitive ELISA assays, enzyme-linked immunospot assays (ELISPOT), fluorescent immunoassay (FIA), chemiluminescent immunoassay, flow cytometry assays, immunohistochemistry, Western blot, and protein-chip assays using for example antibodies, antibody fragments, receptors, ligands, or other agents binding the target analyte. Polyclonal or monoclonal antibodies raised against the Nrf2 protein are produced according to established procedures.

In some embodiments, the Nrf2 protein is detected using a method other than an immunoassay. For example, the miR biogenesis factor(s) can be detected using matrix-assisted laser desorption-ionization time-of-flight mass spectrometry (MALDI-TOF) or protein purification and analysis.

In other embodiments, the level of Nrf2 protein is identified by determining the level of RNA expressing the Nrf2 protein. Methods of determining the level of RNA expression include PCR, and other methods described herein for detecting nucleotides.

Obtaining a Biological Sample

The NRF2 pathway proteins are analyzed in a sample which has been obtained from a subject. A sample, i.e., a biological sample, as used herein, is meant to include any biological sample from a subject that is suitable for analysis of NRF2 pathway proteins. Suitable biological samples include but are not limited to bodily fluids such as blood-related samples (e.g., whole blood, serum, plasma, and other blood-derived samples), urine, sputum, cerebral spinal fluid, bronchoalveolar lavage, and the like. Another example of a biological sample is a tissue sample. In some embodiments, the biological sample is a cancer cell or tissue including cancer cells. Detection of mutation of an NRF2 pathway protein can be determined either in vitro or ex vivo.

The methods involve providing or obtaining a biological sample from the subject, which can be obtained by any known means including needle stick, needle biopsy, swab, and the like. In an exemplary method, the biological sample is a blood sample, which may be obtained for example by venipuncture.

A biological sample may be fresh or stored. Biological samples may be or have been stored or banked under suitable tissue storage conditions. The biological sample may be a tissue sample expressly obtained for the assays of this invention or a tissue sample obtained for another purpose which can be subsampled for the assays of this invention. Preferably, biological samples are either chilled or frozen shortly after collection if they are being stored to prevent deterioration of the sample.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC) or HPLC, or precipitation of apolipoprotein B containing proteins with dextran sulfate or other methods. Any of a number of standard aqueous buffer solutions at physiological pH, such as phosphate, Tris, or the like, can be used.

Radiation Therapy

The method of treating a subject who has been diagnosed with cancer includes the step of treating the subject with radiation therapy if the subject is characterized as being radiation-susceptible, or treating the subject with radiation therapy and a radiosensitizing agent if the subject is characterized as being radioresistant. Radiotherapy may induce cell cycle delay or cell death through DNA damage in the cells by radiation to remove abnormal cells, However, recurrence of cancer may occur due to intrinsic radioresistance of cancer cells, resulting in increased in resistance to radiotherapy.

Radiation-susceptible refers to a subject for whom radiation therapy is therapeutically effective. Radioresistant, on the other hand, refers to a subject for whom radiation shows an inability to kill cancer cells or a substantially reduced ability to kill them. Alternatively, it refers to the case wherein there is no treatment effect from the beginning, or if there is treatment effect at the beginning that is lost during a continuous treatment process.

Radiotherapy may include ionizing radiation, particularly gamma radiation irradiated by commonly used linear accelerators or radionuclides. The radiotherapy to tumor by radionuclides may be achieved externally or internally. Radiotherapy may include brachytherapy, radionuclide therapy, external beam radiation therapy, thermal therapy (cryoablation hyperthermia), radiosurgery, charged-particle radiotherapy, neutron radiotherapy and photodynamic therapy, and the like.

Radiotherapy can be implemented by using a linear accelerator to irradiate the affected part with X-rays or an electron beam. While the X-ray conditions will differ depending on how far the tumor has advanced and its size and the like, a normal dose will be 1.5 to 3 Gy, preferably around 2 Gy, 2 to 5 times a week, and preferably 4 or 5 times a week, over a period of 1 to 5 weeks, for a total dose of 20 to 70 Gy, preferably 40 to 70 Gy, and more preferably 50 to 60 Gy. While the electron beam conditions will also differ depending on how far the tumor has advanced and its size and the like, a normal dose will be 2 to 5 Gy, preferably around 4 Gy, 1 to 5 times a week, and preferably 2 or 3 times a week, over a period of 1 to 5 weeks, for a total dose of 30 to 70 Gy, and preferably 40 to 60 Gy.

Examples of tumors that are radioresistant include tumors that have many hypoxic tumor cells and tumors that have relatively high levels of anti-oxidative enzymes. These tumors are further affected by mutations in proteins in the NRF2 pathway, which plays a role in the protection of cells against oxidative damage. A major problem with cancer radiotherapy is the presence of radioresistant cancer cells. The radioresistant tumor tissues are mostly in hypoxic regions and exhibit resistance to radiotherapy. In a hypoxic state, the radiation-resistance of these cells' to DNA damage induced by the radiation is not fixed by oxygen. Moreover, reactive oxygen species produced in the cancer cells by the radiation are eliminated by anti-oxidative enzymes, making it difficult to induce apoptosis. Specific examples of tumors that are radioresistant include malignant melanomas, malignant glioblastomas and various types of sarcomas such as osteosarcomas, as well as nearly all types of locally advanced neoplasms that have grown to several centimeters or more.

Radiosensitizing Agents

As used herein, a "radiosensitizer" is an agent capable of increasing the sensitivity of cells to radiation in cancer treatment using radiation. A variety of radiosensitizers are known to those skilled in the art. See Karar et al., Cancer Biol Ther. 2009 November; 8(21):1994-2001, the disclosure of which is incorporated herein by reference. The effectiveness of radiotherapy may be increased by administering a radiosensitizing agent in addition to treating a subject with radiation. The present invention makes use of genospecific radiosensitization based on characterization of the genotype of the radioresistance, and administration of a radiosensitizing agent tailored to overcome the type of radioresistance that has developed.

Figure 7:
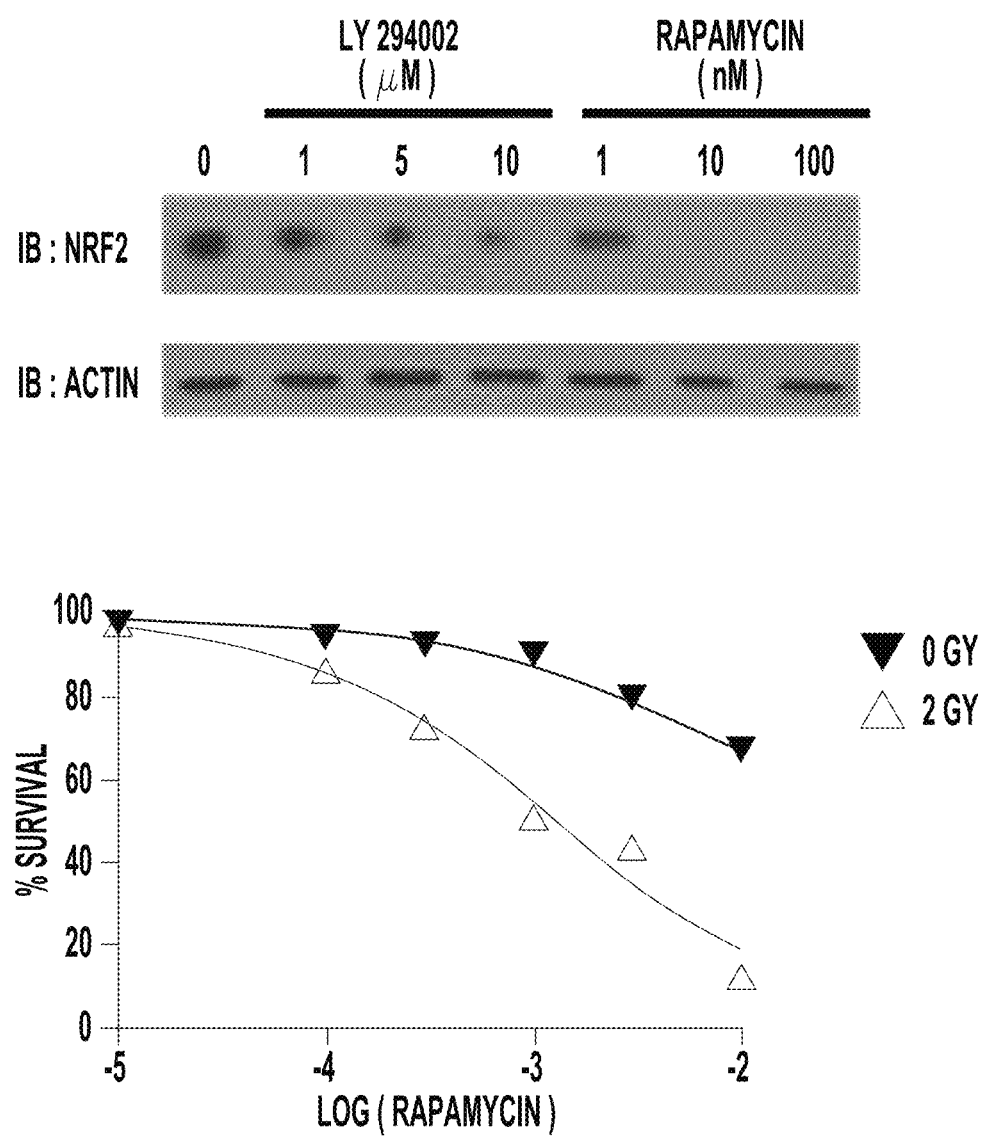
FIG. 7 provides a gel image and a graph showing inhibition of mTOR reverses the functional effects of KEAP1 alterations. Cell line HCC15, which contains a mutation in KEAP1 (G364C), was exposed to increasing doses of the PI3K inhibitor (LY 294002) and mTOR inhibitor (rapamycin). Rapamycin resulted in a more potent reduction in NRF2 levels (top) compared to inhibition of PI3K and effected radiation sensitivity (bottom).

In some embodiments of the invention, the radiosensitizing agent is an mTOR inhibitor. The inventors have shown that the mTOR inhibitor rapamycin degrades NRF2 and effects therapeutic sensitivity in cell lines with KEAP1 mutation. See FIG. 7. Mammalian target of rapamycin (mTOR) is a serine/threonine kinase, which belongs to phosphatidylinositol-3 kinase (PI3K) related kinases (PIKKs) family. It regulates cellular metabolism, growth, and proliferation, and therefore is a target for the development of a number of mTOR inhibitors.

In some embodiments, the mTOR inhibitor is rapamycin. In other embodiments, the mTOR inhibitor is a rapamycin derivatives with improved pharmacokinetics and reduced immunosuppressive effects, referred to as "rapalogs." These rapalogs include temsirolimus (CCI-779), everolimus (RAD001), and ridaforolimus (AP-23573). In further embodiments, a second generation mTOR inhibitor can be used. Second generation mTOR inhibitors include mTORC1/mTORC2 dual inhibitors are designed to compete with ATP in the catalytic site of mTOR. They inhibit all of the kinase-dependent functions of mTORC1 and mTORC2 and therefore, block the feedback activation of PI3K/AKT signaling, unlike rapalogs that only target mTORC1. Dual mTOR/PI3K inhibitors include NVP-BEZ235, BGT226, SF1126, PKI-587 and many more. See Zaytseva et al., Cancer Letters 319 (1): 1-7 (2012), the disclosure of which is incorporated herein by reference.

Candidate radiosensitizing agents may be tested using various methods. In some embodiments, the candidate radiosensitizing agents are evaluated using a high-throughput clonogenic growth assay. In other embodiments, they are evaluated in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

The radiosensitizing agent can be administered to a tumor area prior to irradiation. The composition may be preferably administered one month before the irradiation, particularly 10 days or one week before the irradiation. In addition, it is favorable to continue administration of the composition between the first and the last irradiation. The administration amount of radiosensitizer, amount of irradiation, and intermittency of irradiation may be varied according to parameters including the kind and location of cancer, and patient's response to chemotherapy or radiotherapy.

Inhibitory Nucleic Acids as Radiosensitizers

In some embodiments, the radiosensitizing agent is an inhibitory nucleic acid suitable for inhibiting expression of the mutated NRF2 pathway protein. By "inhibitory nucleic acid" is meant a double stranded RNA, siRNA, shRNA, antisense RNA, RNA aptamers, or ribozymes, or a portion thereof, that when administered to a mammalian cell results in a decrease (e.g., by 10%, 25%, 50%, 75%, or even 90-100%) in the expression of a gene involved in the expression of a mutated NRF2 pathway protein. Typically, a nucleic acid inhibitor comprises at least a portion of a target nucleic acid molecule, or comprises at least a portion of the complementary strand of a target nucleic acid molecule. For example, an inhibitory nucleic acid molecule comprises at least a portion of a nucleic acid involved in the expression of an NRF2 pathway protein described herein.

Nucleic acid molecules useful in the methods of the invention include nucleic acid molecule that encode or are complementary to at least a portion of a NRF2 pathway protein, and in particular a mutant NRF2 pathway protein. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is what is meant is the formation of a double-stranded molecule from two complementary polynucleotide sequences (e.g., of a gene described herein), or portions thereof, under various conditions of stringency. See E.g., Wahl G. M. and S. L. Berger (1987) Methods Enzymol. 152:P399; Kimmel, A. R. (1987) Methods Enzymol. 152: 507.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and more preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. For most applications, washing steps that follow hybridization will also vary in stringency. Hybridization techniques are well known to those skilled in the art, and are described, for example, in Ausubel et al. (Current Protocols in Molecular Biology, Wiley Interscience, New York 2001) and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or a nucleic acid sequence (for example, any one of the nucleic acid sequences described herein). Preferably, such a sequence is at least 60%, at least 80%, at least 85%, at least 90%, at least 95%, or at least 99% identical at the amino acid or nucleic acid level (as appropriate) to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis., BLAST, BESTFIT, GAP, or PILUP/PRETTYBOX programs). Such software matches identical or similar sequences by assigning degrees of homology to various substitutions, delections, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

A composition comprising the radiosensitizer (e.g., an inhibitory nucleic acid) and pharmaceutically acceptable carrier may be applied in any suitable dosage form, and may be formulated and administered in oral or parenteral dosage forms. The administration refers to introducing the pharmaceutical composition to a subject by any appropriate method, and includes delivery of the inhibitory nucleic acid by viral or non-viral techniques or implantation of cells expressing the inhibitory nucleic acid. The composition of the present invention may be administered by various routes including oral or parenteral administration as long as it may reach target tissue, and preferably, it may be locally administered to cancer tissue.

According to one embodiment, the inhibitory nucleic acid may be introduced in the cells using various transformation techniques such as nucleic acid and DEAE-dextran complex, nucleic acid and nucleoprotein complex, nucleic acid and lipid complex, and the like. More specifically, it may be introduced in the cells together with G-fectin, Minis TrasIT-TKO lipophilic reagent, delivery reagent including lipofectin, lipofectamine, cellfectin, cationic phospholipid nanoparticles, cationic polymer, cationic micelle, cationic emulsion or liposome, or biocompatible polymer such as polyethyleneglycol may be conjugated therewith to increase intracellular absorption.

According to another embodiment, the inhibitory nucleic acid may be included in a delivery system enabling efficient intracellular introduction. The delivery system may be preferably a vector, and both viral vector and non-viral vector may be used. The viral vector may include lentivirus, retrovirus, adenovirus, herpes virus and avipox virus vector, and the like may be used, but is not limited thereto.

According to another embodiment, the inhibitory nucleic acid may be introduced in the cells. The cells in which the inhibitory nucleic acid is introduced may express he inhibitory nucleic acid with high level, and by implanting the cells into cancer tissues, radiosensitivity of cancer tissues may be enhanced and radiotherapy effect may be maximized.

Alternately, the inhibitory nucleic acid is a siRNA. siRNA is a duplex RNA which specifically cleaves target molecules to induce RNA interference (RNAi). Preferably, the siRNA of the present invention has a nucleotide sequence composed of a sense RNA strand homologous entirely or partially to a gene expressing a mutant NRF2 pathway protein nucleic acid sequence and an antisense RNA strand complementary thereto, which hybridizes with its target sequence within cells.

In some embodiments, the inhibitory nucleic acid is a RNA aptamer. A RNA aptamer is a nucleic acid ligand which can adopt a specific three-dimensional conformation suitable for binding to target nucleic acid sequences to form a complex therewith, showing an antagonist effect thereon. Typically, the aptamer may be a short nucleic acid molecule 15-50 nt in length which is folded into a predetermined secondary or tertiary structure, e.g., a stem-loop structure. Preferably, aptamers bind at a kd less than $10^{-6}$, $10^{-8}$, $10^{-10}$, or $10^{-12}$ to target molecules. The specificity of the aptamer for target molecules may be very high. Further, the aptamer may consist of a number of ribonucleotide units, deoxyribonucleotide units or a mixture of the two nucleotide units. Also, the aptamer may further comprise one or more modified base, sugar or phosphate backbone units.

In some embodiments, the inhibitory nucleic acid is a ribozyme. A ribozyme is an RNA molecule that catalyzes an intramolecular or intermolecular chemical reaction. Not only nucleases based on ribozymes found in the natural system, but also different types of ribozymes which catalyze similarly to nucleic acid polymerases, such as hammerhead ribozymes, hairpin ribozymes and tetrahymena ribozymes, are also useful in the present invention. Further, although not found in the natural system, the ribozymes engineered to catalyze specific reactions within the cells may also be employed. Ribozymes may cleave RNA or DNA substrates, with a preference for RNA substrates. Typically, a ribozyme recognizes, binds to and then cleaves a target substrate. The recognition is based on base pairing interaction therebetween, allowing for target-specific cleavage.

Determining if a Subject has a History of Tobacco Smoking

Another aspect of the invention provides a method of determining if a subject has a history of tobacco smoking that includes analyzing an NRF2 pathway protein to determine if a mutation is present in suitable sample obtained from the subject, and characterizing the subject as having a history of tobacco smoking if a genetic fingerprint consistent with tobacco exposure is identified. A genetic fingerprint, as used herein, refers to pre-identified levels of a plurality of polypeptides, or the genes involved in their expression, involved in the NRF2 pathway.

Determining if a subject has a history of tobacco smoking can be used to guide treatment of the subject, or can be used for other purposes such as determining the cost of insuring the subject. In some embodiments, the NRF2 pathway protein is KEAP1, while in further embodiments the KEAP1 mutation is a mutation selected from Table 1. In further embodiments, the subject has been diagnosed with cancer, and characterization of the subject's history of tobacco smoking is used to guide selection of a more effective treatment regimen of the cancer. A more effective treatment regimen can include administration of a radiosensitizing agent before or during radiotherapy. A genospecific radiosensitizing agent can also be used. For example, in some embodiments, the radiosensitizing agent is an mTOR inhibitor.

Figure 6:
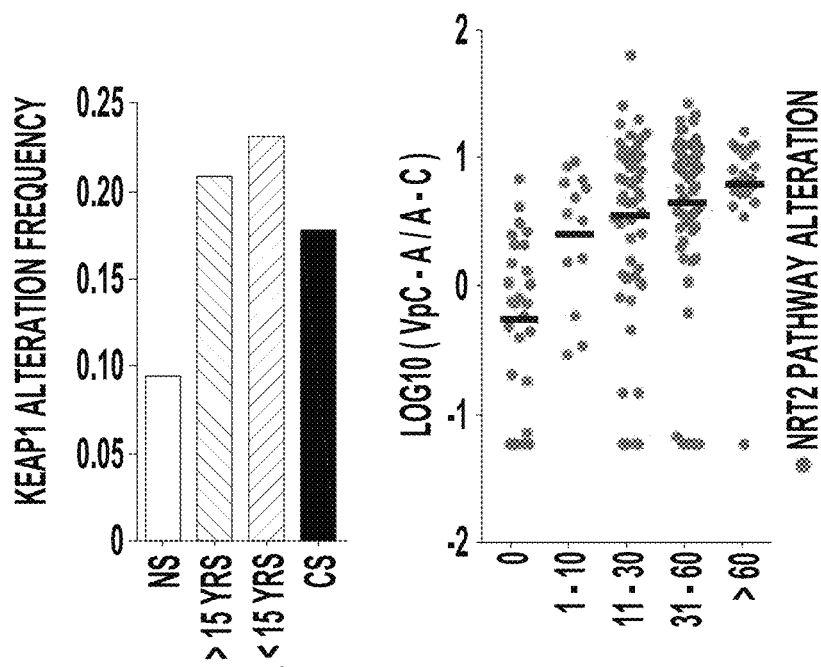
FIG. 6 provides graphs showing KEAP1 alterations are tobacco associated. (Left) The frequency of KEAP1 alteration is higher in reformed and current smokers compared to nonsmokers. (Right) Using a validated smoking metric (y-axis), NRF2 pathway alterations (mainly KEAP1 alterations) are associated with C-to-A genetic transition and by extension tobacco consumption.

The inventors have shown that KEAP1 alterations are tobacco-associated. See FIG. 6. The most dominant cause of lung cancer is tobacco use, but occupational and environmental exposure to various other carcinogenic substances can also influence disease development. In long-term smokers, the risk of lung cancer never returns to the "baseline" level of a never-smoker, even years after smoking cessation. Accordingly, it can be helpful to identify subjects who have a history of tobacco use.

The present invention is illustrated by the following examples. It is to be understood that the particular examples, materials, amounts, and procedures are to be interpreted broadly in accordance with the scope and spirit of the invention as set forth herein.

EXAMPLES

Example 1

Gene Mutations Associated with Radiation Survival

The inventors studied genetic determinants of radiation survival of 535 cancer cell lines across 26 cancer types, with the data all derived from a single experimental platform and analyzed using a rigorous statistical methodology. The results reveal important insights into the intrinsic determinants of cellular response to ionizing radiation.

Gene Mutations and Cellular Survival after Ionizing Irradiation

Recent studies have identified frequent and targetable gene mutations that are correlated with the likelihood of response to specific agents in cancer. Lynch et al., N Engl J Med 350, 2129 (May 20, 2004); Chapman et al., N Engl J Med 364, 2507 (Jun. 30, 2011). Identifying gene mutations that correlate with radiation response have the potential to similarly inform clinical management. The inventors analyzed mutations that conferred radiation resistance and identified the key regulator of oxidative stress response, KEAP1. KEAP1 mutations were ranked ninth (IC=0.112, P=0.0513) from a list of 1610 genes (FIG. 3). The inventors (and others) have shown that mutations in KEAP1 result in the stabilization and activity of the master transcriptional regulator of oxidative damage response, Nrf2 (encoded by NFE2L2), thereby conferring radiation resistance. Taguchi et al., Genes Cells 16, 123 (February, 2011); Zhang et al., Mol Cancer Ther 9, 336 (February, 2010). Recently, the functional spectrum of KEAP1 mutations was analyzed, revealing distinct functional categories including passenger, loss-of-function, hypomorphic, or "super-binders." Hast et al., Cancer Res 74, 808 (Feb. 1, 2014). The likelihood of passenger or hypomorphic mutations masking association was reasoned to be less likely to occur in a lineage with frequent KEAP1 mutations. To test this, the IC in adenocarcinoma of the lung was analyzed. Lung adenocarcinoma has the highest frequency of KEAP1 mutations of any lineage profiled by the TCGA network to date (FIG. 1). N. Cancer Genome Atlas Research, Comprehensive molecular profiling of lung adenocarcinoma. Nature 511, 543 (Jul. 31, 2014). Consistent with TCGA network data, the strongest association between KEAP1 mutation and radiation resistance was in adenocarcinoma of the lung (IC=0.352, P=0.0224) (FIG. 2). CUL3, encoding the ubiquitin ligase adapter that binds to Keap1 and degrades Nrf2, was also associated with radiation resistance in adenocarcinoma of the lung.

To assess the impact of mutation position on the IC, the relative importance of residue position on survival in the binding partner of Keap1, Nrf2, was assessed (FIG. 3). In human cancer, somatic mutations in NFE2L2 frequently occur within the two KEAP1 binding sites ($D_{29}LG$ and $E_{79}TGE$). Shibata et al., Proceedings of the National Academy of Sciences of the United States of America 105, 13568 (Sep. 9, 2008). The IC values for NFE2L2 mutation across all lineages (IC=−0.0697, P=0.329) was significantly higher when only mutations in the two KEAP1 binding sites were considered (IC=0.245, P=0.033).

Taken together, these results describe gene mutation determinants of radiation-induced cellular damage response and reveal distinct functional consequences for categories of mutations within individual genes.

Figure 8:
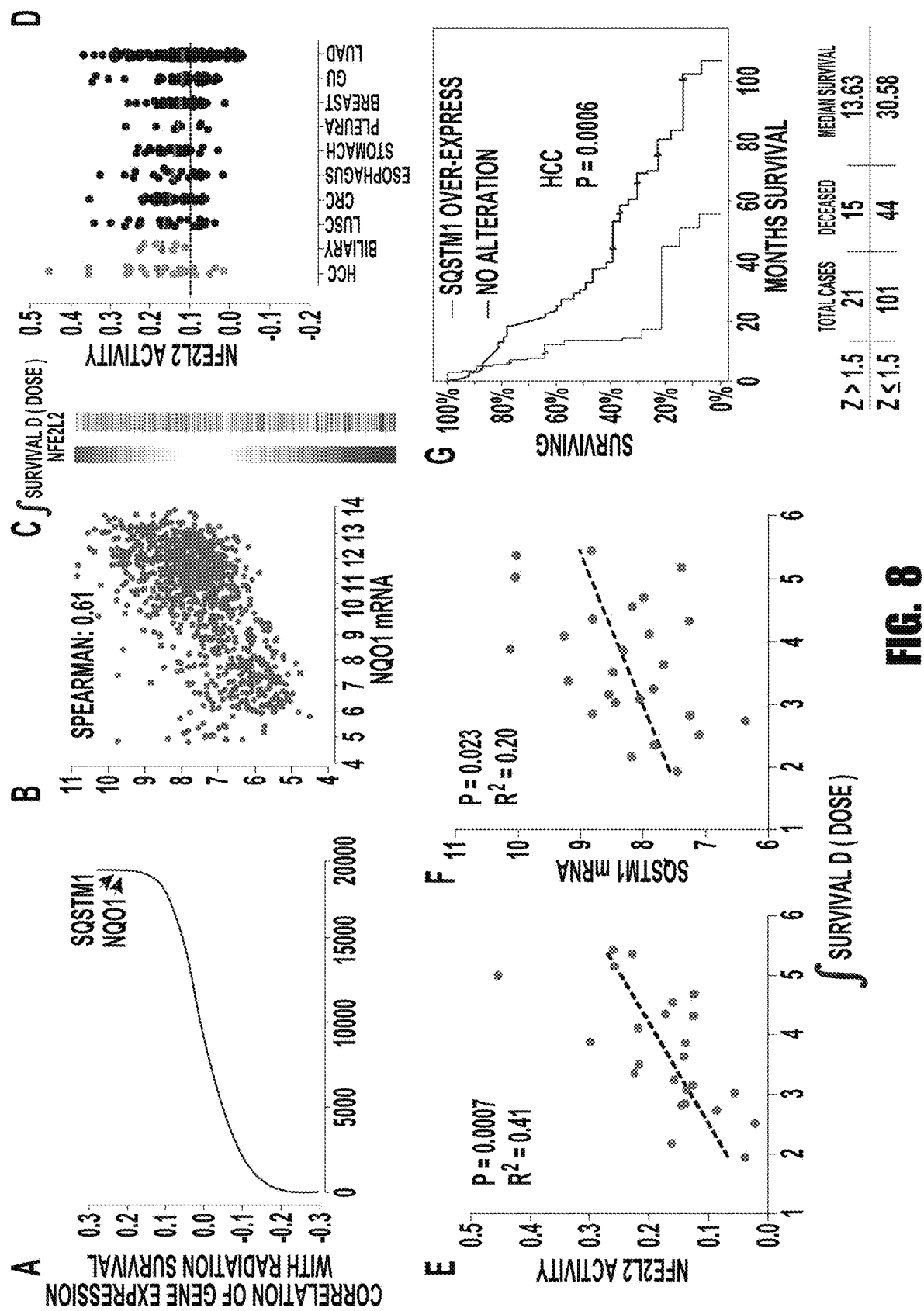
FIG. 8 (A-G) provides graphs showing gene expression changes regulating oxidative stress response are associated with radiation resistance in several cancer lineages. (a) Correlation of NQO1 and SQSTM1 expression with radiation resistance. Spearman correlation coefficient was calculated between gene expression and integral survival values. Correlation was then plotted relative to correlation rank. (b) Relationship between NQO1 and SQSTM1 mRNA expression in CCLE. (c) ssGSEA association between NFE2L2 signature score and integral survival. (d) NFE2L2 is frequently activated in hepatocellular (HCC) and biliary tumors. A column scatter plot of NFE2L2 signature score for 967 cell lines in the CCLE organized by disease site and histology where appropriate. Solid bars represent the mean in each category. Dashed line represents the median across all CCLE lines. (e) NFE2L2 activity scores and (f) SQSTM1 mRNA levels from HCC and biliary cancer cell lines were plotted as a function of radiation integral survival. (g) Kaplan-Meier survival analysis curve calculated from 122 hepatocellular cancer patients from TCGA; cut-off=z>1.5. z=+0.8 or greater demonstrated a statistically significant difference in overall survival by log-rank test.

Gene Expression Analysis Identifies Pathways that Correlate with Survival after Irradiation To assess the importance of the expression of individual genes on radiation survival, we calculated correlation coefficients between 18,988 genes and integral survival values (FIG. 8a). NQO1 and SQSTM1 were the ninth and 11th genes identified as strongly associated with radiation resistance. NQO1 encodes the NAD(P)H-quinone oxidoreductase, an enzyme that detoxifies cells from reactive oxygen species generating quinonoid compounds. Dinkova-Kostova et al., Arch Biochem Biophys 501, 116 (Sep. 1, 2010). SQSTM1 (Sqstm1, p62) is a ubiquitin binding protein that plays a role in oxidative stress, cellular signaling, and autophagy. Mathew et al., Cell 137, 1062 (Jun. 12, 2009). Sqstm1 has been previously been shown to interact with Keap1 and accumulation of Sqstm1 can lead to an increase in Nrf2 activity. Komatsu et al., Nature cell biology 12, 213 (March, 2010). Both NQO1 and SQSTM1 are transcriptionally activated by Nrf2. D. Malhotra et al., Nucleic Acids Res 38, 5718 (September, 2010).

Consistent with these results, NQO1 and SQSTM1 gene expression is strongly correlated across 979 CCLE cell lines (FIG. 8b) and NFE2L2 transcriptional activity is associated with radiation survival across all lineages (FIG. 8c). NFE2L2 transcriptional activity plotted by lineage revealed the highest overall activity in hepatocellular (HCC) and biliary carcinomas (FIG. 8d). The inventors recently showed that Nrf2 is mainly activated by mutations in NFE2L2 and/or KEAP1 and/or deletions in CUL3 in lung squamous cancers (LUSC). M. Abazeed et al., Cancer Res, 15; 73(20): 6289-98 (Aug. 26, 2013). Similar alterations have not been identified in HCC or biliary carcinoma (TCGA network). Instead, recent reports suggest an important role for SQSTM1 in Nrf2 activation in hepatocellular carcinomas. Komatsu et al., Nature cell biology 12, 213 (March, 2010). To test the test the association between Nrf2 and Sqstm1 activity and radiation survival in HCC, integral survival values were plotted with NFE2L2 activity (FIG. 8e) and SQSTM1 expression (FIG. 8f). It was found that HCC had the strongest association between radiation survival and Nrf2 activity in any lineage profiled ($R^2$=0.41 in HCC v. $R^2$=0.22 in LUSC). SQSTM1 expression was also correlated with radiation survival. However, the extent of correlation was lower than that obtained with the Nrf2 score. This is likely attributed to noise associated with single gene expression measurements compared to a composite Nrf2 score that includes 567 genes. HCC is routinely managed by gene toxic therapies (chemo- and/or radio-embolization, external beam radiotherapy) and/or surgery, suggesting that patients that resist gene toxic stress may have poorer clinical outcomes. HCC patients with elevated SQSTM1 expression have a significantly lower overall survival, indicating a poor overall prognosis for patients with active Nrf2 in HCC (FIG. 8g) (TCGA network). This is analogous to the poor prognosis of NSCLC patients with active Nrf2.

Example II

NRF2 Activation Predicts for Response to Radiotherapy

Figure 9:
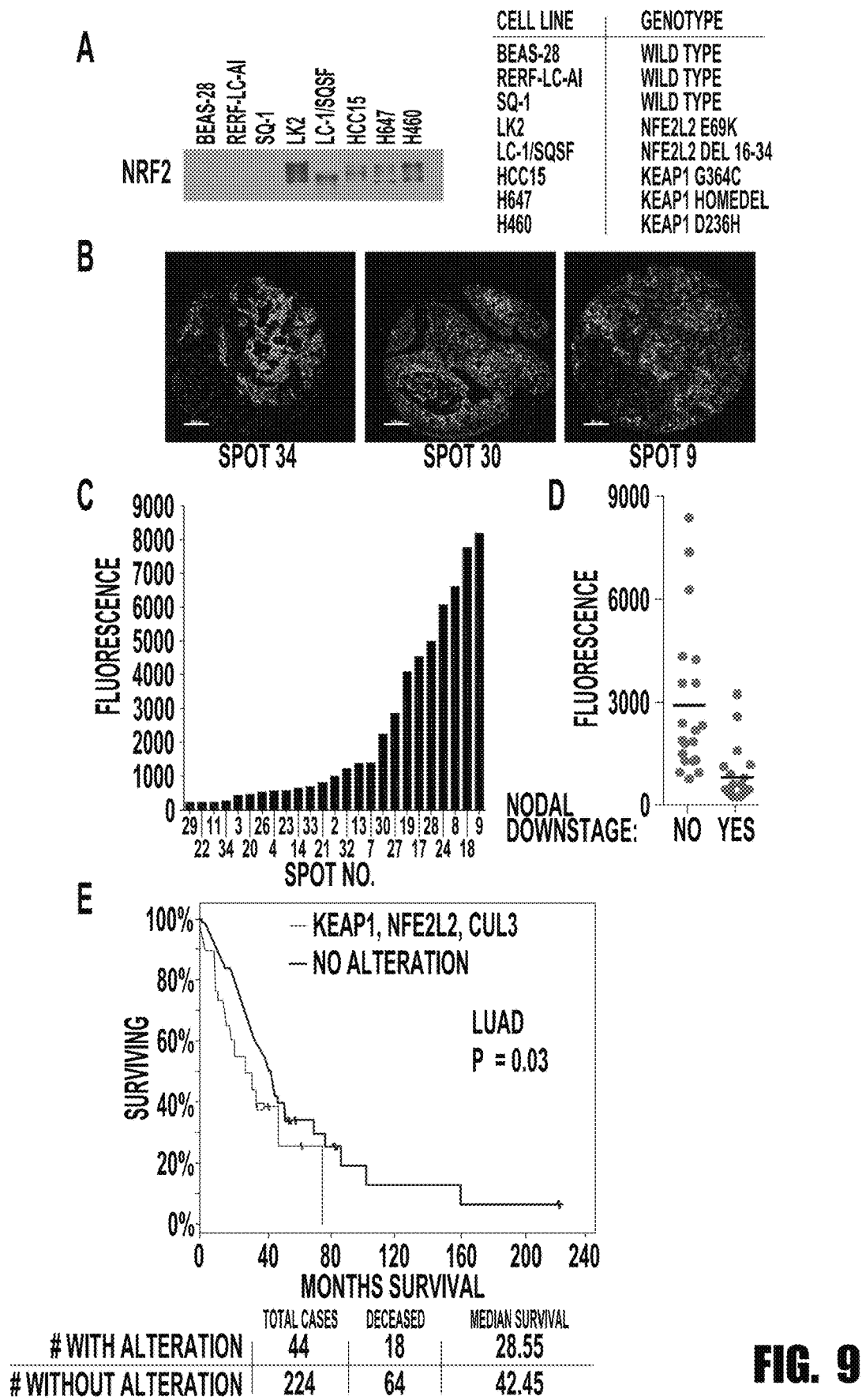
FIG. 9 (A-E) provides graphs and images showing NRF2 activation predicts for response to radiotherapy: (a) Cell lines with genetic alterations in NFE2L2 or KEAP1 have elevated levels of Nrf2 protein. α-Nrf2 antibody clone D1Z9C specifically identifies Nrf2 as measured by Western blot. Nrf2 expression is elevated in a subset of NSCLC TMA test spots. (b) Immunofluorescence image using DAPI, cytokeratin, and Nrf2, demonstrating a TMA sample with low, moderate, and elevated Nrf2 expression. (c) Fluorescence score extracted from a TMA test set demonstrating that ~24% of this NSCLC test set has "elevated" Nrf2 levels (cutoff of 1000). This is largely consistent with more recent genomic data that indicates the frequency of NFE2L2 and KEAP1 alterations to represent 15-25% of NSCLC. (d) Fluorescence score derived from patients who received chemotherapy and radiation followed surgery and segregated by whether they had a decreased lymph node burden of disease after therapy. Patients with elevated fluoresence values were less likely to respond to therapy. P=0.0001. (e) Lung cancer patients with alterations in NFE2L2, KEAP1, or CUL3 have a shorter median survival than patients without alterations.

The inventors sought to develop accurate and robust NFE2L2-activity based molecular diagnostics that incorporates the biologic outcomes of mutations in NFE2L2 and KEAP1 and deletion of CUL3, namely the stabilization of NRF2. Based on their data, measurement of NRF2 protein levels in treatment naïve patient samples is likely to reflect pathway activation. To achieve this, they implemented a quantitative immunofluorescence capability. The inventors first validated that a monoclonal antibody against Nrf2 (Clone D1Z9C)) is specific and correlates with mutations in NFE2L2 and KEAP1 (FIG. 9a). They then developed a scaled tissue microarray consisting of 100 spots in two-fold redundancy derived from tissue of patients with stage IIIA NSCLC patients treated with tri-modality therapy (induction chemotherapy and radiation followed by surgery). All patients underwent a PET/CT staging scan and mediastinoscopy prior to treatment. CT, PET/CT, mediastinoscopy, and post-surgical pathologic tumor staging along with other pertinent clinical parameters were annotated. Titer levels were first optimized, and expression of Nrf2 evaluated using quantitative immunofluorescence (IF) in the scaled tissue microarray. We then measured Nrf2 levels on the assembled TMA (FIGS. 9b and 9c). The degree of Nrf2 activation by IF was largely consistent with our genomic data that indicates the frequency of NFE2L2 and KEAP1 alterations to represent 17-30% of NSCLC. Multiple clinical endpoints were reflected on the degree of NRF2 IF. NRF2 is a predictor of nodal response in locally advanced NSCLC (FIG. 9d).

There was a trend toward greater primary tumor size response in the low NRF2 arm (cutoff NRF2 IF=432, P=0.07, data not shown). In a separate cohort comprised of NSCLC patients with all stages of disease (I-IV), TCGA data was augmented by directed profiling for NFE2L2, KEAP1, and CUL3 alterations of an additional 108 patients. K-M survival curves were plotted based on the presence or absence of genetic alterations in the three genes. Activation of NFE2L2 results in a decrement in overall survival.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating a subject who has been diagnosed with cancer, the method comprising:
   (a) analyzing a NFE2L2 pathway protein in a biological sample obtained from the subject;
   (b) characterizing the subject as radiation-susceptible if the NFE2L2 pathway protein does not include a mutation, or characterizing the subject as radioresistant if the NFE2L2 pathway protein includes a mutation; and
   (c) treating the subject with radiation therapy if the subject is characterized as being radiation-susceptible, or treating the subject with radiation therapy and an mTOR inhibitor if the subject is characterized as being radioresistant.

2. The method of claim 1, wherein analyzing the NFE2L2 pathway protein further comprises determining a level of the NFE2L2 pathway protein in the biological sample obtained from the subject, wherein an elevated level of the NFE2L2 pathway protein also characterizes the subject as being radioresistant.

3. The method of claim 2, wherein the level of NRF2 protein is determined using an immunoassay.

4. The method of claim 1, wherein the cancer is lung adenocarcinoma.

5. The method of claim 1, wherein the subject is human.

6. The method of claim 5, wherein the subject has a history of long-term tobacco smoking.

7. The method of claim 1, wherein the mutation is detected using PCR analysis.

* * * * *